(12) United States Patent
Fleizach et al.

(10) Patent No.: US 12,627,329 B2
(45) Date of Patent: May 12, 2026

(54) LOW PROBABILITY OF INTERCEPT SIGNAL INTERCEPTOR BUOY

(71) Applicant: The United States of America, as represented by the Secretary of the Navy, Arlington, VA (US)

(72) Inventors: Gregory Knowles Fleizach, San Diego, CA (US); Barry R. Hunt, San Diego, CA (US); Doug Kenneth Herbers, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 347 days.

(21) Appl. No.: 18/588,878

(22) Filed: Feb. 27, 2024

(65) Prior Publication Data

US 2025/0274158 A1 Aug. 28, 2025

(51) Int. Cl.
*H04B 1/40* (2015.01)
*B63B 22/00* (2006.01)
(Continued)

(52) U.S. Cl.
CPC .............. *H04B 1/40* (2013.01); *B63B 22/00* (2013.01); *G01N 33/1886* (2013.01); *B63B 2211/02* (2013.01); *H04B 2001/3894* (2013.01)

(58) Field of Classification Search
CPC .............. H04B 1/40; H04B 1/44; H04B 1/48; H04B 1/59; B63B 22/00; G01N 33/1886; G01N 2211/02; G01N 2001/3894
(Continued)

(56) References Cited

U.S. PATENT DOCUMENTS

| 10,640,177 | B1 * | 5/2020 | Robertson | ............... B63B 22/18 |
| 10,697,777 | B1 * | 6/2020 | Robertson | ............ G01C 21/203 |

(Continued)

FOREIGN PATENT DOCUMENTS

| CA | 3008370 A1 * | 4/2019 | .......... G01S 5/0246 |
| CN | 103618555 A * | 3/2014 | |

(Continued)

OTHER PUBLICATIONS

P. A. Lessing et al.; Use of the Automatic Identification System (AIS) on Autonomous Weather Buoys for Maritime Domain Awareness Applications; OCEANS 2006, Boston, MA, USA, 2006, pp. 1-6, doi: 10.1109/OCEANS.2006.307023.
(Continued)

*Primary Examiner* — Jean A Gelin
(74) *Attorney, Agent, or Firm* — Naval Information Warfare Center Pacific; Kyle Eppele; J. Eric Anderson

(57) ABSTRACT

A sensor buoy comprising: a buoy casing configured to float on a body of water; an antenna mounted to the buoy casing so as to limit an RF range of view to no more than fifteen kilometers; an instantaneous frequency measurement (IFM) receiver mounted to the buoy casing and communicatively coupled to the antenna; a pulse descriptor word (PDW) generator mounted to the buoy casing and configured to receive an output from the IFM receiver; a processor configured to receive PDWs generated by the PDW generator and to calculate a corresponding pulse repetition interval (PRI); a magnetometer communicatively coupled to the processor; a scheduler communicatively coupled to the processor and configured to control when the sensor buoy transmits information; and a transmitter communicatively coupled to the scheduler and configured to format data from the processor into a correct format and packet structure for transmission.

20 Claims, 5 Drawing Sheets

(51) Int. Cl.
  G01N 33/18  (2006.01)
  H04B 1/38  (2015.01)
(58) Field of Classification Search
  USPC ....................................................... 455/452.1
  See application file for complete search history.

(56)  References Cited

U.S. PATENT DOCUMENTS

| | | | | |
|---|---|---|---|---|
| 2004/0229531 A1* | 11/2004 | Driscoll | ................. | B63B 21/48 |
| | | | | 441/25 |
| 2014/0210658 A1* | 7/2014 | Ponsford | ................. | G08G 3/02 |
| | | | | 342/41 |
| 2015/0346726 A1* | 12/2015 | Davoodi | ................. | B63B 22/20 |
| | | | | 440/38 |
| 2021/0276729 A1* | 9/2021 | Sundararaj | ............. | B64C 35/00 |
| 2022/0316939 A1* | 10/2022 | Tian | ......................... | G01F 25/20 |
| 2023/0406468 A1* | 12/2023 | Price | ...................... | B63C 11/26 |
| 2025/0102295 A1* | 3/2025 | Binder | ................... | G01S 15/08 |
| 2025/0102487 A1* | 3/2025 | Elliott | .................... | B63B 22/00 |
| 2025/0157623 A1* | 5/2025 | Kurani | .................. | A61B 5/411 |

FOREIGN PATENT DOCUMENTS

| | | | | | | |
|---|---|---|---|---|---|---|
| CN | 209896240 | U | * | 1/2020 | | |
| CN | 111210608 | A | * | 5/2020 | ............. | G08C 19/00 |
| CN | 212433393 | U | * | 1/2021 | | |
| CN | 114385272 | A | * | 4/2022 | ......... | G06F 9/44594 |
| EP | 2856203 | B1 | * | 11/2019 | .......... | G01S 7/2923 |
| JP | 2023120796 | A | * | 8/2023 | | |
| KR | 102166842 | B1 | * | 10/2020 | ............. | G01S 15/08 |
| KR | 102500055 | B1 | * | 2/2023 | ............. | B63B 22/24 |
| KR | 20240125101 | A | * | 8/2024 | ............. | G01R 33/02 |
| KR | 20240138765 | A | * | 9/2024 | ............. | G01V 1/186 |
| KR | 102830583 | B1 | * | 7/2025 | ............. | G06T 11/26 |
| WO | WO-2010047931 | A1 | * | 4/2010 | ............. | G01S 7/285 |

OTHER PUBLICATIONS

McLennan, Neil; Spotter Platform; Website description of Spotter buoy commercial product; available at: https://www.sofarocean.com/products/spotter; accessed Jan. 30, 2024.

* cited by examiner

50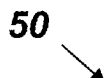

Provide a buoyant buoy casing equipped with a magnetometer and a GPS tracker which are communicatively coupled to a processor, which is mounted to the buoy casing. — 50ₐ

Mount an electrically small antenna to the buoy casing in a position so as to provide a limited reception range of no more than fifteen kilometers. — 50_b

Receive RF signals from an emitter with the antenna. — 50_c

Determine characteristics of the RF signals with the processor. — 50_d

Establish a rough geolocation the size of the limited reception range of the emitter based on detection of the RF signal alone. — 50_e

Transmit the RF signal characteristics and the corresponding rough geolocation of the emitter via satellite to a remote user. — 50_f

*Fig. 4*

LOW PROBABILITY OF INTERCEPT SIGNAL INTERCEPTOR BUOY

FEDERALLY-SPONSORED RESEARCH AND DEVELOPMENT

The United States Government has ownership rights in the invention claimed herein. Licensing and technical inquiries may be directed to the Office of Research and Technical Applications, Naval Information Warfare Center Pacific, Code 72110, San Diego, CA, 92152; voice (619) 553-5118; NIWC_Pacific_T2@us.navy.mil. Reference Navy Case Number 210997.

BACKGROUND OF THE INVENTION

Maritime domain awareness (MDA) is the effective understanding of anything associated with the maritime domain that could impact the security, safety, economy, or environment. Transmissions from a given vessel, such as automatic identification system (AIS) signals, may be used to identify the given vessel's location, among other data to improve MDA. However, some transmissions are low power or otherwise difficult to detect. There is a need for a way to improve MDA.

SUMMARY

Disclosed herein is a sensor buoy comprising a buoy casing, an antenna, an instantaneous frequency measurement (IFM) receiver, a pulse descriptor word (PDW) generator, a processor, a magnetometer, a scheduler, and a transmitter. The buoy casing is configured to float on a body of water. The antenna is electrically small and mounted to the buoy casing so as to limit a radio frequency (RF) range of view to no more than fifteen kilometers. The IFM receiver is mounted to the buoy casing and communicatively coupled to the antenna. The PDW generator is mounted to the buoy casing and configured to receive an output from the IFM receiver. The processor is configured to receive PDWs generated by the PDW generator and to calculate a corresponding pulse repetition interval (PRI). The magnetometer is communicatively coupled to the processor. The scheduler is communicatively coupled to the processor and configured to control when the sensor buoy transmits information. The transmitter is communicatively coupled to the scheduler and configured to format data from the processor into a correct format and packet structure for transmission.

Also disclosed herein is a method for increasing maritime domain awareness comprising the following steps. The first step involves providing a buoy casing configured to float on a body of water. The buoy casing is equipped with a global positioning system (GPS) tracker and a magnetometer, both of which are communicatively coupled to a processor which is mounted to the buoy casing. Another step provides for mounting an electrically small antenna to the buoy casing in a position so as to provide a limited RF reception range of no more than fifteen kilometers. Another step provides for receiving RF signals from an emitter with the antenna. Another step provides for determining characteristics of the RF signals with the processor. Another step provides for establishing a rough geolocation the size of the limited reception range of the emitter based on detection of the RF signal alone. Another step provides for transmitting the RF signal characteristics and the corresponding rough geolocation of the emitter via satellite to a remote user.

BRIEF DESCRIPTION OF THE DRAWINGS

Throughout the several views, like elements are referenced using like references. The elements in the figures are not drawn to scale and some dimensions are exaggerated for clarity.

FIG. 4 is a flowchart.

DETAILED DESCRIPTION OF EMBODIMENTS

The disclosed buoy and methods below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

Figure 1A:
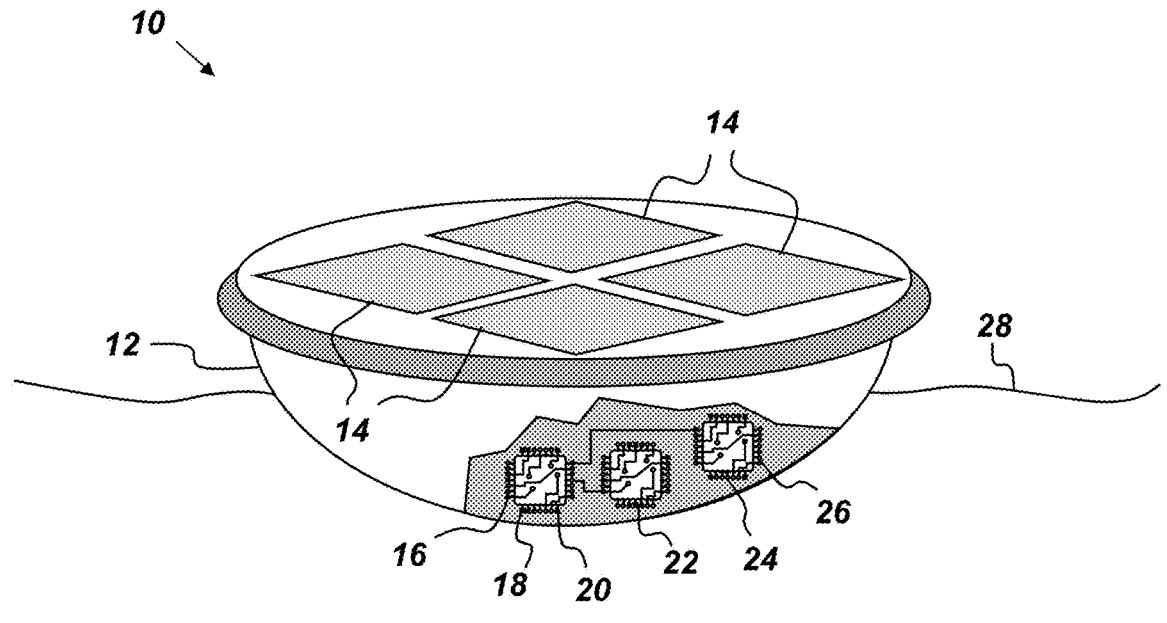
FIG. 1A is a perspective-view illustration of an embodiment of a sensor buoy.
Figure 1B:
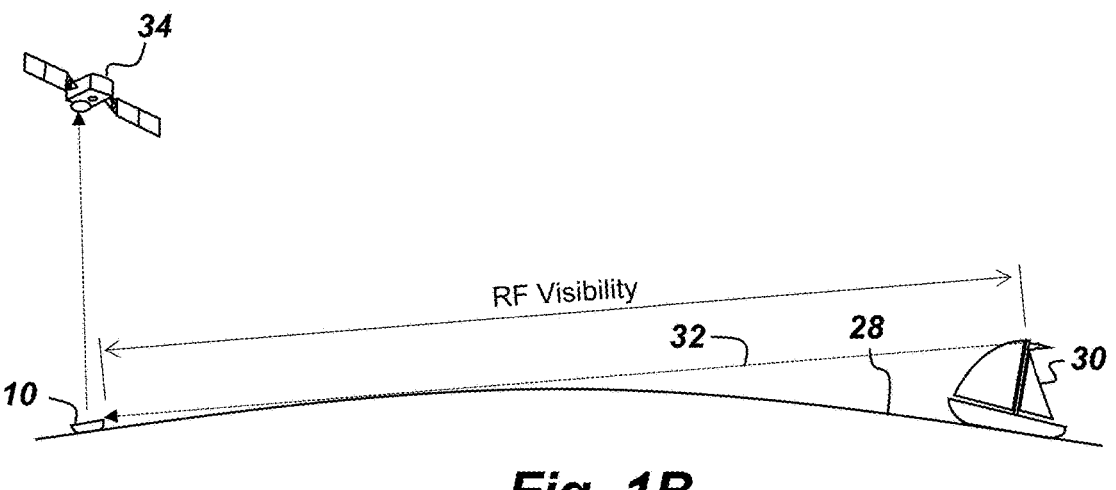
FIG. 1B is a side-view illustration of a sensor buoy and a vessel on a water surface.

FIG. 1A is a perspective-view illustration of an embodiment of a sensor buoy 10 that comprises, consists of, or consists essentially of a buoy casing 12, an electrically small antenna 14, an IFM receiver 16, a PDW generator 18, a processor 20, a magnetometer 22, a scheduler 24, and a transmitter 26. The buoy casing 12 is configured to float on a surface 28 of a body of water. FIG. 1B is a side-view illustration of the sensor buoy 10 on the water surface 28. In this embodiment of the sensor buoy 10, the antenna 14 comprises four receive antennas that have approximately 90° horizontal beamwidths and are mounted to the buoy casing 12 so as to provide a limited RF range of view of no more than fifteen kilometers. The antenna 14 may be horizontally polarized. Suitable examples of the antenna 14 include, but are not limited to, a patch antenna, a whip antenna, and an e-field probe. In the sensor buoy 10 embodiment shown in FIG. 1A, the limited RF reception range limits the sensor buoy 10's RF visibility to vessels 30 of desired height. For example, in one embodiment, the receive antenna(s) 14 may be mounted to the buoy casing 12 at a height of just 0.25 meters above the water surface 28 so that that the sensor buoy 10 would have a limited RF visibility/horizon of no more than ten kilometers to an emitter three meters above the water surface 28 (such as is shown in FIG. 1B where the vessel 30 represents a small craft having a low power transmitter mounted three meters above the water surface). In the embodiment of the sensor buoy 10 where the receive antenna(s) 14 are mounted 0.25 meters above the water surface 28, the sensor buoy 10 would have an RF visibility of approximately fifteen kilometers to an emitter ten meters above the water surface 28 (e.g. larger vessel).

Still referring to FIGS. 1A and 1B, the IFM receiver 16 is mounted to the buoy casing 12 and is communicatively coupled to the four receive antennas 14. The PDW generator 18 is also mounted to the buoy casing 12 and is configured to receive an output from the IFM receiver 16. The processor 20 is configured to receive PDWs generated by the PDW generator 18 and to calculate a corresponding pulse repetition interval (PRI) for signals 32 received from distant emitters (e.g. vessel 30). Instead of transmitting PDWs as soon as they are received, the sensor buoy 10 can store results in memory and wait for a query signal. Upon receiving a query signal, the sensor buoy 10 may be configured to send back all its results at once to maximize transmitter sleep time. The processor 20 can be programmed to look for signals matching certain parameters. For example, only signals in a certain frequency range, matching a pulse width, or with a specific scan rate could be reported. The magnetometer 22 is communicatively coupled to the processor 20. The scheduler 24 is communicatively coupled to the processor 20 and is configured to control when the sensor buoy 10 transmits information. The transmitter 26 is communicatively coupled to the scheduler 24 and configured to format data from the processor into a correct format and packet structure for transmission. The antenna 14 may comprise N receive antennas with approximately 360°/N horizontal beamwidths positioned to function as sector antennas. In the embodiment of the sensor buoy 10 shown in FIG. 1A, the four receive antennas 14 are quadrant antennas and the buoy casing 12 is an untethered drifting/free-floating buoy. The buoy casing 12 may also be a station-keeping buoy depending on the desired operational scenario.

The sensor buoy 10 may be used to improve the detection of low probability of intercept (LPI) emitters and other hard-to-detect signals to improve MDA. Examples of LPI emitters include, but are not limited to, emitters that use low peak power (LPP) transmissions, class-B AIS transponders, emitters that employ antenna sidelobe reductions, and very high frequency (VHF) transmitters. The accuracy of parameter estimation for a detected signal is tied to signal-to-noise ratio (SNR). In other words, the more signal power received, the easier it is to correctly estimate signal parameters. When signals are received at the threshold of detection, the parameter estimates will be sub-optimal. Sometimes it is not possible to detect LPP signals at all because they are received at or below the receiver noise floor. As such, LPI signals can easily be missed. Class-B AIS signals, similar to LPP radar signals, are very low power, and the VHF signal propagation is limited to line of sight. As a result, stand-off interception of these signals can be difficult. For example, satellite collection of AIS signals is more difficult for class-B signals, and in dense areas, the huge field of view from a satellite can cause pulse collisions at the satellite receiver. The result is that the detection of these signals from space can be difficult if not impossible in some situations. Moreover, many AIS collectors do not cover high latitudes at all. The sensor buoy 10 addresses these challenges by having a purposefully-limited RF range of view such that if another vessel 30 is within range, the sensor buoy 10 should be able to receive its signal without interference from other signal emitters that are farther away.

Embodiments of the sensor buoy 10 can be made to have very small physical dimensions (e.g., smaller than 8000 cm³). The sensor buoy 10 can be made with low-sensitivity, low power electronics (e.g., IFM receiver), which allow the sensor buoy 10 to be more readily disposable than larger, more expensive RF receiver solutions. Physically small embodiments of the sensor buoy 10 may be emplaced in areas that larger platforms might not be able to go. Also, large numbers of the sensor buoy 10 may be placed in areas close to probable locations of LPI emitters of interest. The buoy casing 12 keeps the sensor buoy 10 afloat and oriented vertically. Ideally, the receive antenna(s) 14 will be mounted to near the top of the buoy casing 12, which is purposefully not very high so as to limit the incoming signals the sensor buoy 10 may receive. Limiting the height of the receive antenna(s) 14 on the buoy casing 12 limits the radar horizon, or RF range of view of the sensor buoy 10. It is also desirable to place the receive antenna(s) 14 as far from the water surface 28 as possible to reduce multipath reflections while still maintaining the limited RF range of view of fifteen kilometers.

Figure 2:
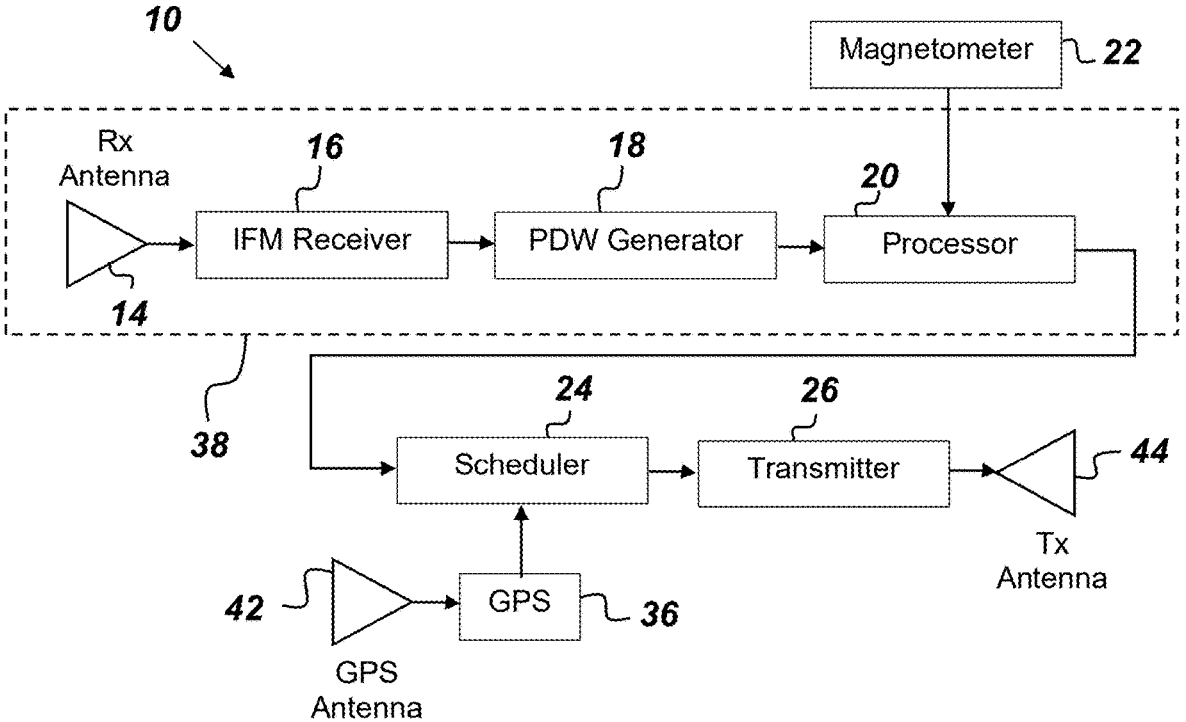
FIG. 2 is a block diagram of an embodiment of a sensor buoy.

FIG. 2 is a block diagram of an embodiment of the sensor buoy 10. The IFM receiver 16 is used to detect signals received by the receive antennas 14. IFM receivers cover wide bandwidths and quickly measure frequency of input signals. IFM receivers were designed to allow the measurement of frequency with minimal complexity, which means that IFM receivers can be low cost and consume very little power. The information from the IFM receiver 16 may be fed to the PDW generator 18 to capture signal characteristics in a condensed format including RF, pulse width, and time of arrival (TOA). A disadvantage of IFM receivers is that they are not accurate in the presence of multiple signals. The small radar horizon/RF visibility will limit the pulse collisions and allow the IFM receiver 16 to report accurate pulse measurements. The sensor buoy 10's radar horizon $r_{km}$ may be approximated according to the following equation: $r_{km}=4.1*(\sqrt{h_{1,m}}+\sqrt{h_{2,m}})$ where $h_{1,m}$ is the height of the receive antenna(s) 14 from the water surface 28 and $h_{2,m}$ is the height of an emitter from the water surface 28. In some embodiments, it may be desirable for the magnetometer 22 to comprise a 3-axis accelerometer and to configure the processor 20 to factor wave height of a given wave supporting the sensor buoy 10 (as measured by the 3-axis accelerometer) into the calculation of the rough geolocation.

The processor 20 may be configured to take the PDWs and generate PRIs, which can be used to further characterize LPI emitters. A simple version of a PRI identifier measures the time between TOAs for adjacent pulses at the same frequency. Additionally, scan rate from azimuth-rotating radars can be determined from the fluctuating power levels received by the receive antennas 14. Because the sensor buoy's radar horizon is relatively small, the detection of an RF signal itself provides a rough geolocation of the corresponding emitter. That is, the observed emitter is within, say, a radius of ten kilometers around the global positioning system (GPS) location of the sensor buoy 10. In embodiments of the sensor buoy 10 where the buoy casing 12 is untethered and at the mercy of winds and currents, the magnetometer 22 may be used to identify magnetic North and report the sector in which the signal was detected (e.g. North=315° to 45° in azimuth, East=45° to 135°, etc.). Note that from magnetic North and GPS location, it is possible to approximate true North.

The processor 20 may be configured to use the angle of arrival (AOA) to further refine the geolocation estimate of the emitter. For example, for a ten kilometers radar horizon, the area visible by sensor buoy 10 is approximately 314 km². Restricting that area to one sector reduces the area in which the emitter could be to about 80 km², equivalent to an ellipse with a semi-major axis of ten kilometers and a semi-minor axis of 2.5 kilometers. This is a very respectable geolocation estimate, particularly for an LPP emitter. The output of the processor 20 may be a full intercept report (aka contact report) with RF, pulse width, TOA, PRI, scan rate, and geolocation. Even if the processor 20 is only able to output a subset of the aforementioned parameters, this would still be useful particularly for hard to detect LPI signals. The processor 20 may be configured to generate small-sized intercept reports (i.e., less than a kilobyte). For example, a small intercept report of ~100 bytes could still include data on ten different PRIs. One can expect a relatively low number of intercepts at the sensor buoy 10 given the limited RF visibility due to the short mounting height and nature of the receive antenna(s) 14.

The scheduler 24 controls when the sensor buoy 10 will exfiltrate results via transmission, such as to a satellite 34, as shown in FIG. 1B. Accurate time can come from an onboard GPS device 36. The time for transmission may be controlled to limit transmissions during certain periods or to wait for a certain number of detections to be accumulated (e.g. to improve link efficiency since there is some amount of overhead associated with each transmission). For near-real-time use, a minimum transmittal rate could be set (e.g. every ten minutes). The targets for the sensor buoy 10 are signals that cannot be reliably detected with other assets. For the types of signals the sensor buoy 10 may be configured to detect, a transmission schedule with a latency on the order of hours or days may not be impractical.

The transmitter 24 formats the data into the correct format and packet structure for transmission. The most practical transmission channel for the open ocean scenario of interest is via satellite. The clear view to the sky and the small RF signal horizon from the sensor buoy 10 also makes satellite communications an ideal choice. There are many potential satellite systems that can accommodate a relatively small amount of data (i.e., few intercept reports, each of which are ~100 bytes). One example is the Iridium Short Burst Data (SBD) messaging service.

Not shown above in FIGS. 1A, 1B, and 2 is a power source, but since the sensor buoy 10 is meant to be on open water with a clear view of the sky, solar power is an obvious choice. Paired with a battery to maintain power overnight and through cloudy stretches, the sensor buoy 10 is capable of running nearly indefinitely. Based on the size of the solar panels (such as the solar panels 46 shown in FIG. 3) and battery, the processor 20 and scheduler 24 may be configured to work together to manage the sensor buoy's power since transmissions of data from the sensor buoy 10 would be the primary power consumer. Compared with satellite systems with huge antenna footprints that can see thousands of emitters at once, the small radar horizon of the sensor buoy 10 is an advantage. Because the number of emitters that will be within fifteen kilometers of the sensor buoy 10 is comparatively small, the processor 20 does not have to be exceptionally powerful to deinterleave the visible signals. Moreover, the probability that observable signals will be overlapping with each other is low. This means that the inexpensive IFM receivers are ideally suited to the task.

The above description focused largely on LPI emitters, but other modular receiver payloads could be included such as an AIS receiver. For example, the IFM receiver 16 and the PDW generator 18 may be replaced by, or supplemented by, an AIS receiver communicatively coupled to the processor 20. AIS collectors on shore can only see so far out to sea, beyond which they cannot collect AIS signals. Additionally, there are areas of the world not covered by commercial AIS satellite collectors, such as very high latitudes. In these areas, it would be advantageous to use the sensor buoy 10 as a local AIS collector that can receive, process, and relay information via separate transmission channels. The sensor buoy 10 can be configured to downsample received AIS transmissions so the transmitter 24 is not retransmitting received AIS messages every few seconds but at much lower rates such as transmitting every several minutes or even hours. One embodiment of the sensor buoy 10 may be configured to base its rough geolocation estimate of a given vessel 30 (i.e., being within its fifteen kilometer RF range of view) on detection of a wireless fidelity (Wi-Fi) signal from the given vessel 30.

The sensor buoy 10 may be configured to capture the location, speed, and direction of movement of a ship or small craft, but not necessarily the precise ship/craft track. A received AIS signal may also have extraneous data that is not necessary to re-transmit. For example, the sensor buoy 10 can be configured to just transmit the position-related data vice the whole message. For a given AIS transmission that does not include position data, the processor 20 may be configured to exfiltrate relevant identifying information about the given AIS transmission and the location of the sensor buoy 10 with its limited radar horizon so as to provide a coarse geolocation of the corresponding transmitter of the given AIS transmission, as described above.

Figure 3:
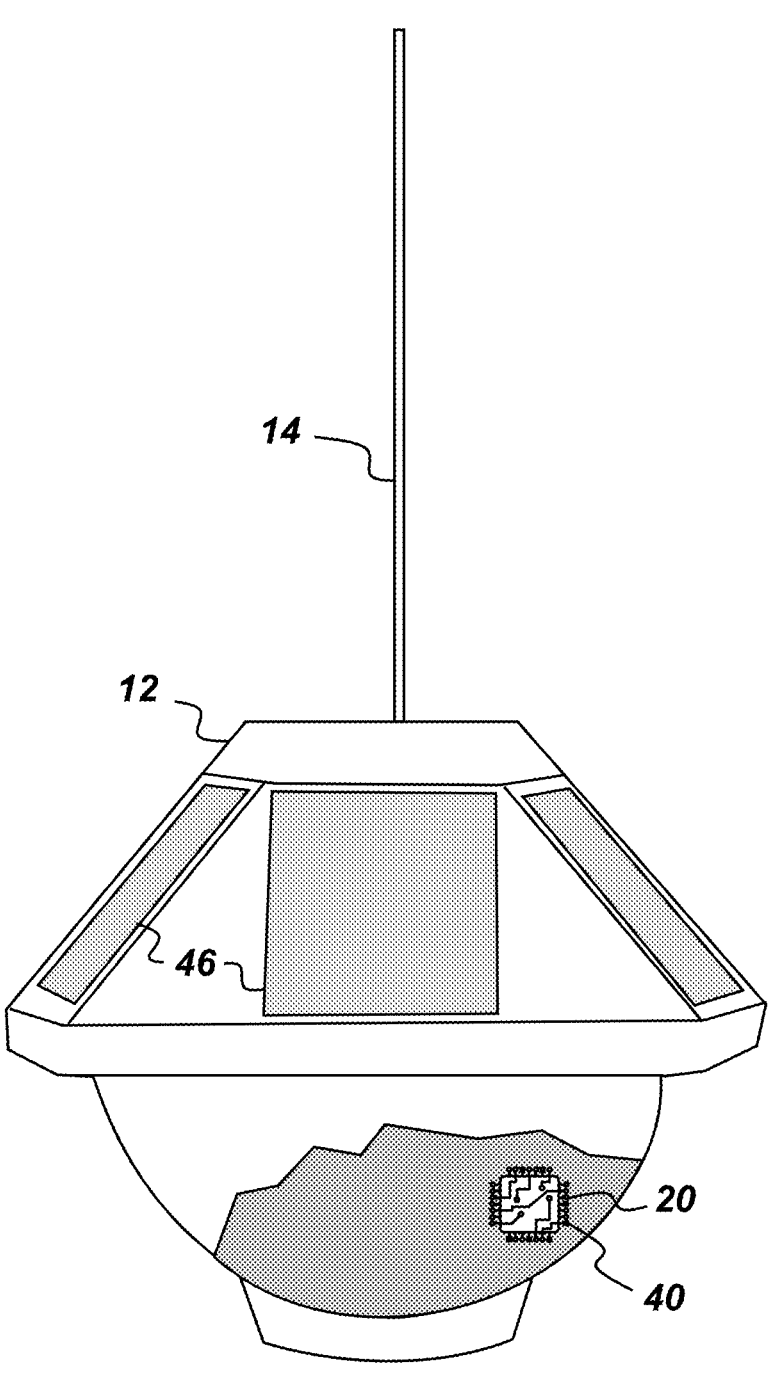
FIG. 3 is a side-view illustration of an embodiment of a sensor buoy.

FIG. 3 is a side-view illustration of an embodiment of the sensor buoy 10 where the IFM receiver 16 and the PDW generator 18 shown in FIG. 1A are replaced by a VHF receiver 40 operatively coupled to the processor 20 and to the receive antenna 14, which in this embodiment is a whip antenna to detect VHF transmissions. For these particular transmissions, the content of the message may not necessarily be needed, but just the frequency channel number and transmission length can provide useful information. For example, any transmissions on channel sixteen are considered an emergency. The sensor buoy 10 may be configured such that received VHF signals on channel sixteen (indicating an emergency) trigger an immediate exfiltration. Similarly, the interception of a specific emitter (e.g., based on RF, pulse width, PRI, and/or scan rate) might also trigger an immediate exfiltration of the data. The VHF channel number could also help identify patterns, and even type or nationality of a vessel. For example, if it is known what channel a certain nation's fishing fleet transmits on, those detections could be noted. VHF radio waves are not strongly reflected from the atmosphere like the waves from lower frequencies and as a result, the waves do not readily travel beyond the horizon. The inability of VHF waves to pass through hills and other large structures further limits their range. Depending on the mission set, a certain receiver payload 38 (e.g., AIS receiver, VHF receiver, etc.) may be selected. Different receiver payloads 38 may be used that conform to a specific form factor to fit within or on the buoy casing 12, that have an electrical interface for receiving power from the sensor buoy 10, and that are configured to pass on results to the exfiltration transmitter 24. Additionally, each receiver payload 38 may be configured to have its own receive antenna(s) 14. For example, whip antennas make the most sense for the AIS and VHF payloads because of the long wavelengths (on the order of meters) at these frequency ranges. Patch antennas are practical for detecting radar signals in the S- and X-bands. It is desirable for whip antennas to be vertically-oriented and for both the GPS and transmit antennas, 42 and 44 respectively, to be pointed toward the sky. FIG. 3 also depicts solar panels 46.

FIG. 4 is a flowchart of a method 50 for increasing maritime domain awareness comprising the following steps. The first step 50ₐ involves providing a buoyant buoy casing equipped with a magnetometer and a GPS tracker which are communicatively coupled to a processor, which is mounted to the buoy casing. Another step 50_b provides for mounting an electrically small antenna to the buoy casing in a position so as to provide a limited reception range of no more than fifteen kilometers. Another step 50_c provides for receiving RF signals from an emitter with the antenna. Another step $50_d$ provides for determining characteristics of the RF signals with the processor. Another step $50_e$ provides for establishing a rough geolocation the size of the limited reception range of the emitter based on detection of the RF signal alone. Another step $50_f$ provides for transmitting the RF signal characteristics and the corresponding rough geolocation of the emitter via satellite to a remote user.

Sensor buoy 10 enables a semi-consistent detection capability because the sensor buoy 10 can be an access point to continuously monitor an area for extended periods. Therefore, it is possible to learn behaviors and identify patterns of life (given that the sensor buoy 10 may be made to be relatively stationary). Satellites will only detect signals if a given vessel is transmitting during overflight. For S- and X-band radar, it is likely the satellite will detect those signals because they tend to operate continuously, but for VHF/UHF communications they may not be detected if the radio is not in use when the satellite is overhead. The sensor buoy 10 may be configured to transmit its stored data when satellites are overhead. Moreover, there are situations where vessels may turn radar off when in sensitive areas to avoid detection. Thus it may be advantageous to place the sensor buoy 10 on the edge of a sensitive area (e.g., marine preserve, exclusive economic zone, etc.) where the sensor buoy 10 can provide continuous detect capability.

The sensor buoy 10 may also be implemented on a number of different platforms including, but not limited to, unmanned underwater glider, wind-powered maritime drone, and land-based platforms. Further, the sensor buoy 10 can be programmed to look for only AIS reports from certain AIS transmitters for subsequent retransmission. Note that several of the components shown in FIG. 2, such as the scheduler 24 and the processor 20, may be embodied in the same microcontroller, FPGA, etc. However, for modularity purposes, they may also be distinct components. The sensor buoy 10 may have a sleep mode to power down many of its electronics when it does not detect any signals. That is, there is no need to power much of the sensor buoy 10 if there are no signals present. These sleep hours could be configured prior to emplacement or configured remotely. Instead of transmitting on a schedule, the sensor buoy 10 may have a command input pathway via a receive antenna. This could allow the exfiltration of results to occur on a different schedule or only when queried. It would also allow the sensor buoy 10 to be powered on/off remotely. Potentially, a command could be used to scuttle the sensor buoy 10 if needed.

Figure 5:
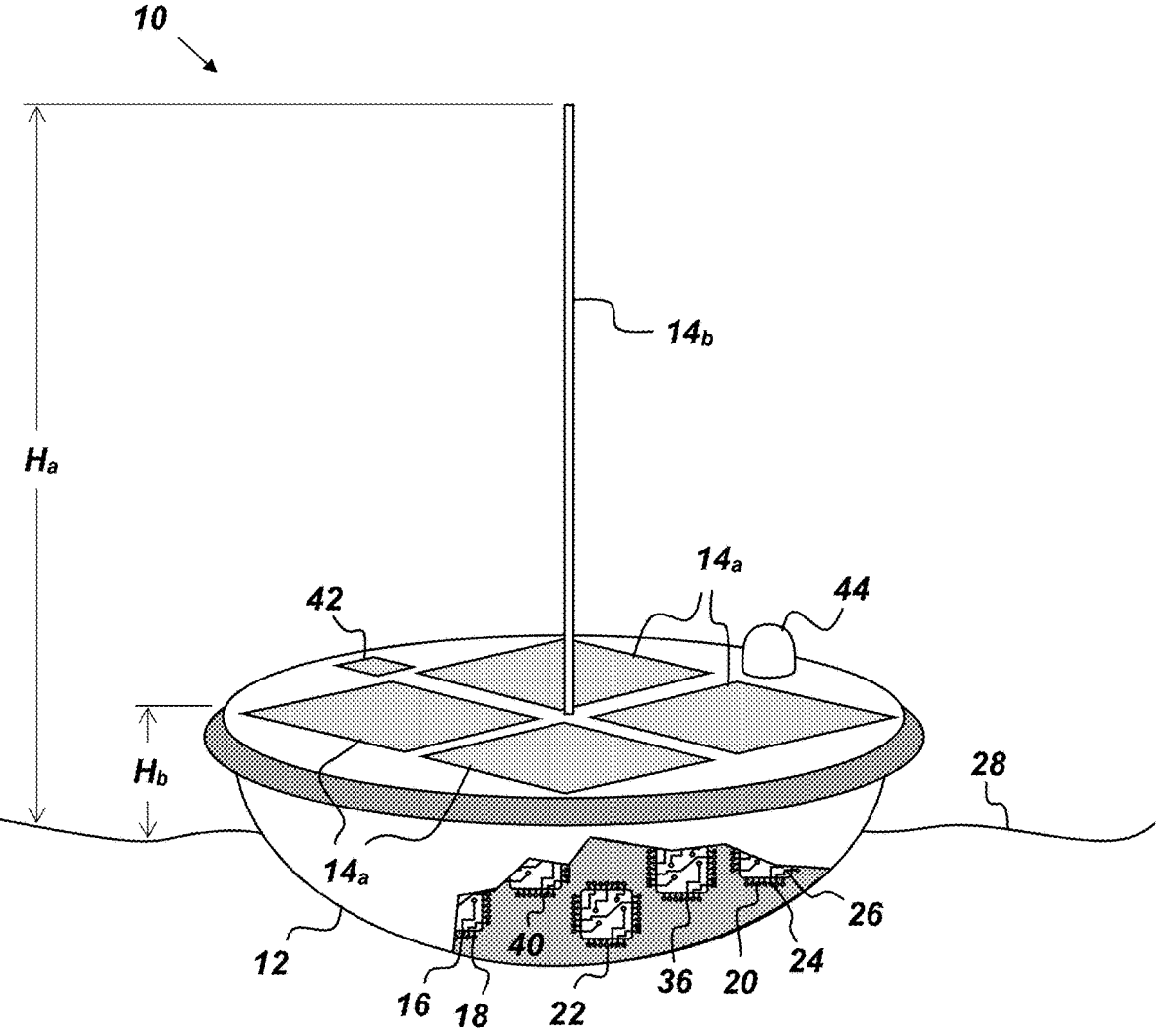
FIG. 5 is a perspective-view illustration of an embodiment of a sensor buoy.

FIG. 5 is a perspective-view illustration of an embodiment of the sensor buoy 10 comprising, consisting, or consisting essentially of the components shown in FIG. 1A, but where the receive antenna 14 comprises four patch antennas $14_a$ and a whip antenna $14_b$. The height $H_a$ of the patch antennas $14_a$ is kept low to purposefully limit the radar horizon of the sensor buoy 10 to no more than fifteen kilometers. Likewise, the height $H_b$ of the whip antenna $14_b$ is also kept low to purposefully limit the line of sight of the sensor buoy 10. For example, the height $H_a$ and the height $H_b$ may be limited to provide an RF range of view of no more than fifteen kilometers. The embodiment of the sensor buoy 10 shown in FIG. 5 represents a stacked implementation that can receive multiple signals at a time. The processor 20 in this implementation is configured to perform correlation of the received intercepts (i.e. RF, AIS, or VHF). Raw data might be more useful to data consumers, but to minimize transmission time and save energy, the intercept data may be processed into tracks. This edge processing requires more compute power on the buoy, but since transmissions typically consume the most energy, the trade-off would be acceptable.

From the above description of the sensor buoy 10 and the method 50 for increasing maritime domain awareness, it is manifest that various techniques may be used for implementing the concepts of the sensor buoy 10 and the method 50 without departing from the scope of the claims. The described embodiments are to be considered in all respects as illustrative and not restrictive. The method/apparatus disclosed herein may be practiced in the absence of any element that is not specifically claimed and/or disclosed herein. It should also be understood that the sensor buoy 10 and the method 50 are not limited to the particular embodiments described herein, but is capable of many embodiments without departing from the scope of the claims.

We claim:

1. A sensor buoy comprising:
   a buoy casing configured to float on a body of water;
   an antenna that is electrically small and mounted to the buoy casing so as to limit an RF range of view to no more than fifteen kilometers;
   an instantaneous frequency measurement (IFM) receiver mounted to the buoy casing and communicatively coupled to the antenna;
   a pulse descriptor word (PDW) generator mounted to the buoy casing and configured to receive an output from the IFM receiver;
   a processor configured to receive PDWs generated by the PDW generator and to calculate a corresponding pulse repetition interval (PRI);
   a magnetometer communicatively coupled to the processor;
   a scheduler communicatively coupled to the processor and configured to control when the sensor buoy transmits information; and
   a transmitter communicatively coupled to the scheduler and configured to format data from the processor into a correct format and packet structure for transmission.

2. The sensor buoy of claim 1, wherein the antenna comprises N receive antennas with approximately 360°/N horizontal beamwidths positioned to function as sector antennas.

3. The sensor buoy of claim 2, wherein the buoy casing is an untethered drifting buoy.

4. The sensor buoy of claim 2, wherein the buoy casing is a station-keeping buoy.

5. The sensor buoy of claim 2, wherein the receive antennas are mounted on the buoy casing above a surface of the body of water but no greater than 0.25 meters above the surface so as to limit the senor buoy's radar horizon, with respect to a distant emitter ten meters above the surface, to no more than fifteen kilometers.

6. The sensor buoy of claim 5, wherein the transmitter is capable of transmitting packets to an Earth satellite.

7. The sensor buoy of claim 6, wherein the processor is further configured to calculate the PRI based on a measured time between time of arrivals for adjacent pulses at a same frequency.

8. A method for increasing maritime domain awareness comprising:
   providing a buoy casing configured to float on a body of water, wherein the buoy casing is equipped with a global positioning system (GPS) tracker and a magnetometer, both of which being communicatively coupled to a processor which is mounted to the buoy casing;

mounting an electrically small antenna to the buoy casing in a position so as to provide a limited RF reception range of no more than fifteen kilometers, wherein the antenna is horizontally polarized; receiving RF signals from an emitter with the antenna; determining characteristics of the RF signals with the processor, wherein the determining characteristics of the RF signals further comprises:

measuring a frequency of each of the RF signals with an instantaneous frequency measurement (IFM) receiver;

feeding an output of the IFM receiver to a pulse descriptor word (PDW) generator to generate PDWs corresponding to the RF signals;

establishing a rough geolocation the size of the limited reception range of the emitter based on detection of the RF signal alone; and transmitting the RF signal characteristics and the corresponding rough geolocation of the emitter via satellite to a remote user.

9. The method of claim 8, wherein the step of determining characteristics of the RF signals further comprises:

measuring a time between time of arrivals (TOAs) for adjacent RF signal pulses having the same frequency.

10. The method of claim 9, wherein the antenna comprises N receive antennas having 360°/N horizontal beamwidths.

11. The method of claim 10, further comprising establishing with the processor a better geolocation of the emitter based on an angle-of-arrival (AOA) of the RF signals and a radar horizon of the N receive antennas.

12. The method of claim 11, wherein the step of determining characteristics of the RF signals further comprises determining a scan rate from azimuth-rotating radars on the emitter by monitoring fluctuating RF signal power levels received by the N receive antennas.

13. The method of claim 12, further comprising using a scheduler communicatively coupled to the processor to control when the transmitting step is performed such that transmissions are sent according to a schedule.

14. The method of claim 13, wherein the schedule limits transmissions to once a day.

15. The method of claim 8, wherein the antenna is a whip antenna capable of receiving very high frequency (VHF) signals, and further comprising performing the transmitting step immediately upon receiving a channel sixteen VHF signal.

16. The method of claim 8, wherein the RF signal is a class-B automatic identification system (AIS) signal.

17. The method of claim 8, wherein the buoy casing is configured to be a station-keeping buoy and is positioned in an ocean at an edge of a sensitive area.

18. The method of claim 8, wherein the antenna is mounted to the buoy casing at approximately 0.25 meters above a surface of the body of water.

19. The method of claim 8, wherein the RF signal is a Wi-Fi signal from another vessel.

20. The method of claim 8, wherein the antenna comprises a whip antenna and N receive antennas having 360°/N horizontal beamwidths.

* * * * *